United States Patent [19]

Singh et al.

[11] Patent Number: 5,523,483
[45] Date of Patent: Jun. 4, 1996

[54] INTEGRATED UREA/AMMONIA PROCESS

[75] Inventors: Vishnu D. Singh, Houston; Meghji N. Shah, Sugarland; Richard B. Strait, Kingwood, all of Tex.

[73] Assignee: The M. W. Kellogg Company, Houston, Tex.

[21] Appl. No.: 490,929

[22] Filed: Jun. 16, 1995

[51] Int. Cl.⁶ .................................................. C07C 273/10
[52] U.S. Cl. .................................................. 564/68; 564/69
[58] Field of Search .......................................... 564/68, 69

[56] References Cited

U.S. PATENT DOCUMENTS

| | | | |
|---|---|---|---|
| 4,055,628 | 10/1977 | McCarroll et al. | 423/448 |
| 4,122,040 | 10/1978 | McCarroll et al. | 252/447 |
| 4,163,775 | 8/1979 | Foster et al. | 423/363 |
| 4,568,530 | 2/1986 | Mandelik et al. | 423/359 |
| 4,568,531 | 2/1986 | van Dijk et al. | 423/361 |
| 4,568,532 | 2/1986 | Benner et al. | 423/361 |
| 5,176,800 | 1/1993 | Zardi et al. | 203/31 |
| 5,223,238 | 6/1993 | Czuppon et al. | 423/359 |

*Primary Examiner*—Peter O'Sullivan
*Attorney, Agent, or Firm*—The M. W. Kellogg Company

[57] ABSTRACT

An integrated ammonia/urea process and a plant for carrying out the same. The process comprises recycling a high pressure purge stream made up mostly of air from the urea synthesis cycle to the autothermal reformer in a syngas production unit of the ammonia process. In such a manner, compression energy required for ammonia synthesis can be reduced since a portion of the high pressure air feed to the autothermal reactor is supplied by the urea purge stream recycle. In addition, the equipment needed to clean up the urea purge stream is largely eliminated.

8 Claims, 2 Drawing Sheets

INTEGRATED UREA/AMMONIA PROCESS

FIELD OF THE INVENTION

The present invention relates to an integrated ammonia/urea process and more particularly to an integrated ammonia/urea process wherein a purge stream from the urea process is supplied as a feedstock to the ammonia process.

BACKGROUND OF THE INVENTION

It is well known in the art to use air for corrosion prevention in a urea process wherein oxygen contained therein passivates the equipment metal surfaces. It is also well known that in most instances the $CO_2$ feed supplied to a urea process contains hydrogen and nitrogen. Typically, air is added to the $CO_2$ feed supplied to the urea reactor. In some urea processes the hydrogen contained in the $CO_2$ feed is reacted with oxygen in the air injected into the process. In other processes the hydrogen remains in the process and is an inert which must be purged from the process along with nitrogen from the air and other inerts. In an integrated process, a portion of the high pressure air compressed for synthesis gas preparation in ammonia production is diverted for metal passivation in urea production. It can be seen that a large quantity of inerts in the reaction feed stream must then be purged from the reaction effluent stream.

A high pressure vapor purge stream removed from the urea synthesis reactor also contains unreacted carbon dioxide and ammonia. Such residuals are substantially absorbed as carbamate in a scrubber employing an aqueous carbamate wash and operating at the synthesis cycle pressure. Purge vapor removed from the high pressure scrubber comprising mostly nitrogen and residual ammonia is generally let down to a medium pressure absorber. The medium pressure absorber employs a plant condensate wash to reduce residual ammonia concentration in the purge vapor to a level suitable for venting to the atmosphere.

It would be advantageous in terms of energy and capital savings to avoid depressurization of the high pressure urea synthesis purge stream and the need for equipment required to remove residual ammonia for atmospheric disposal.

SUMMARY OF THE INVENTION

High pressure purge gas removed from a urea synthesis cycle is recycled to an air feed line upstream of an ammonia plant autothermal or secondary reformer. In such a manner, a portion of the air feed to the ammonia synthesis cycle can be supplemented by urea purge gas saving compression energy of the air compressor and obviating ammonia removal equipment to clean the urea purge stream for atmospheric disposal.

As a first embodiment, the present invention provides an integrated ammonia/urea plant. An ammonia syngas unit, including in series primary and autothermal reformers, a shift converter, a condensate stripper and a $CO_2$ removal unit, is provided for reacting a hydrocarbon feedstock with steam and air and forming a $CO_2$ stream and a syngas makeup stream comprising hydrogen and nitrogen. An ammonia conversion unit including a synthesis loop is provided for mixing a recycle stream with the syngas makeup stream to form an ammonia converter feed stream. In addition, ammonia synthesis loop steps include feeding the ammonia converter feed stream to an ammonia synthesis reactor, recovering an ammonia stream from effluent from the synthesis reactor, recovering a purge stream from the effluent stream, and forming the recycle stream. A urea unit is provided for reacting the $CO_2$ stream with the ammonia stream to form urea at a relatively high pressure in the presence of a passivating amount of oxygen and a minor amount of nitrogen. The urea unit includes a high pressure scrubber for separating oxygen and nitrogen from a urea-containing stream to form a high pressure nitrogen stream containing minor amounts of oxygen, $CO_2$ and ammonia. A line is provided for introducing the high pressure nitrogen stream with compressed air to the autothermal reformer.

The high pressure nitrogen line preferably feeds directly into a compressed air line downstream of an air compressor, and the pressure in the high pressure nitrogen line is greater than the pressure of the compressed air line. The urea unit is preferably free of ammonia removal equipment for treating the high pressure nitrogen stream and free of atmospheric vents for nitrogen from the high pressure scrubber.

As another embodiment, the present invention provides a method for integrating the operation of ammonia and urea plants. The ammonia plant comprises an ammonia syngas unit including in series primary and autothermal reformers, a shift converter, a condensate stripper and a $CO_2$ removal unit, for reacting a hydrocarbon feedstock with steam and air to form a $CO_2$ stream and a syngas makeup stream comprising hydrogen and nitrogen. An ammonia conversion unit includes a synthesis loop for mixing a recycle stream with the syngas makeup stream to form an ammonia converter feed stream, feeding the ammonia converter feed stream to an ammonia synthesis reactor, recovering an ammonia stream from effluent from the synthesis reactor, recovering a purge stream from the effluent stream, and forming the recycle stream. The urea plant comprises a urea unit for reacting the $CO_2$ stream with the ammonia stream to form urea at a relatively high pressure in the presence of a passivating amount of oxygen and a minor amount of nitrogen. The urea unit includes a high pressure scrubber for separating oxygen and nitrogen from a urea-containing stream to form a high pressure nitrogen stream containing minor amounts of oxygen and $CO_2$. The method comprises the step of introducing the high pressure nitrogen stream with compressed air to the autothermal reformer.

The high pressure nitrogen stream in the ammonia/urea integration method preferably supplies at least 1 percent of the nitrogen supplied to the autothermal reformer. The urea unit is preferably free of atmospheric venting of process nitrogen streams. The high pressure scrubber is preferably operated at a higher pressure than the autothermal reformer, and the high pressure nitrogen stream is fed directly into a compressed air line downstream from a discharge of an air compressor and upstream from the autothermal reformer. The high pressure nitrogen stream preferably contains at least 70 mole percent nitrogen, 1–15 mole percent oxygen, 1–15 mole percent ammonia, 1–10 mole percent $CO_2$, up to 3 mole percent water, and less than 100 ppmv hydrogen.

DETAILED DESCRIPTION OF THE INVENTION

Recycle of a high pressure, nitrogen-rich urea synthesis purge stream, otherwise vented to the atmosphere, as a feedstock to an ammonia plant, saves process compression energy required for ammonia synthesis and obviates the need to clean up the urea purge stream.

Figure 1:
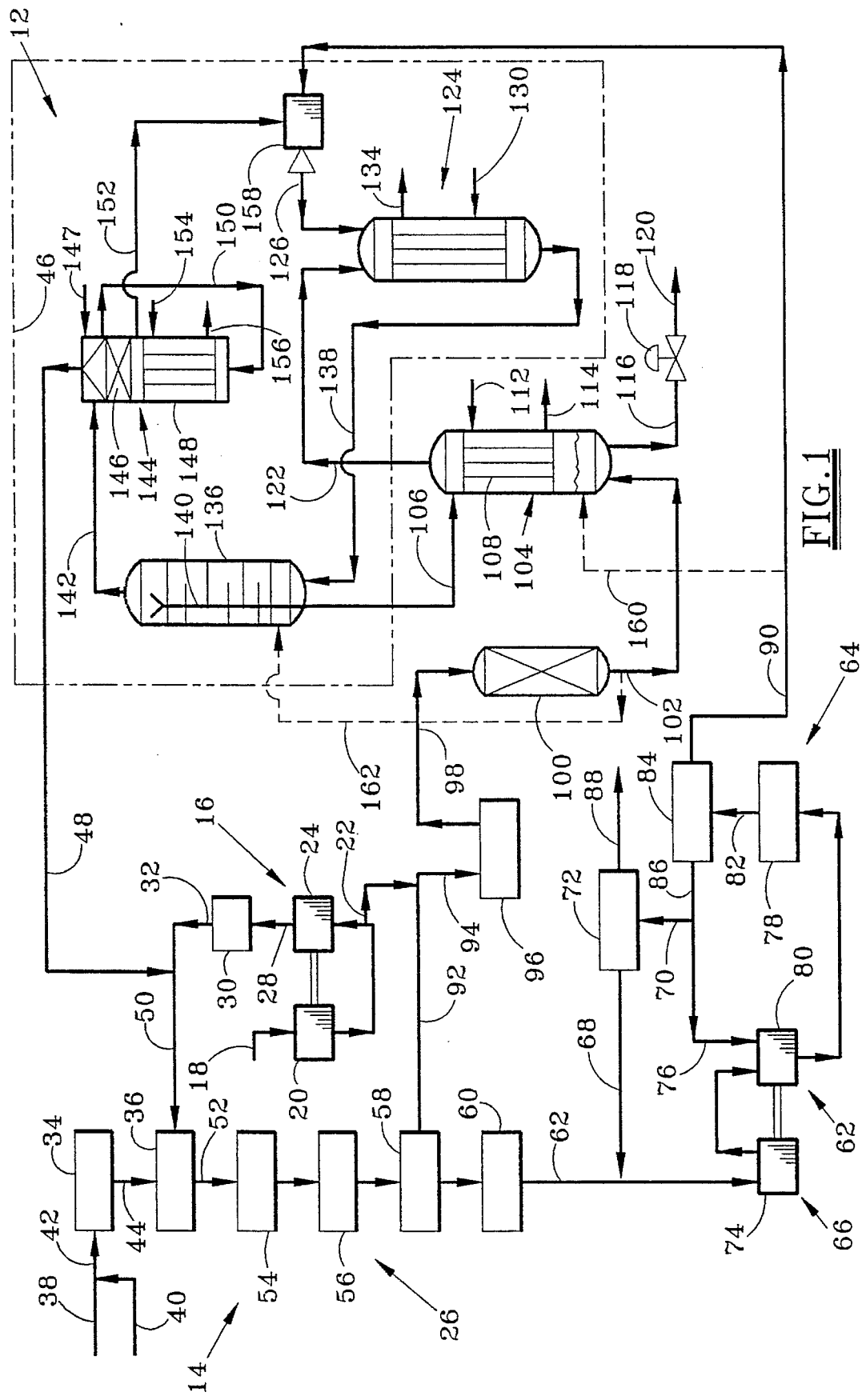
FIG. 1 is a schematic diagram of the integrated ammonia/urea process of the present invention showing a high pressure urea synthesis unit purge stream recycled to an air inlet stream of an ammonia syngas unit autothermal reformer.
Figure 2:
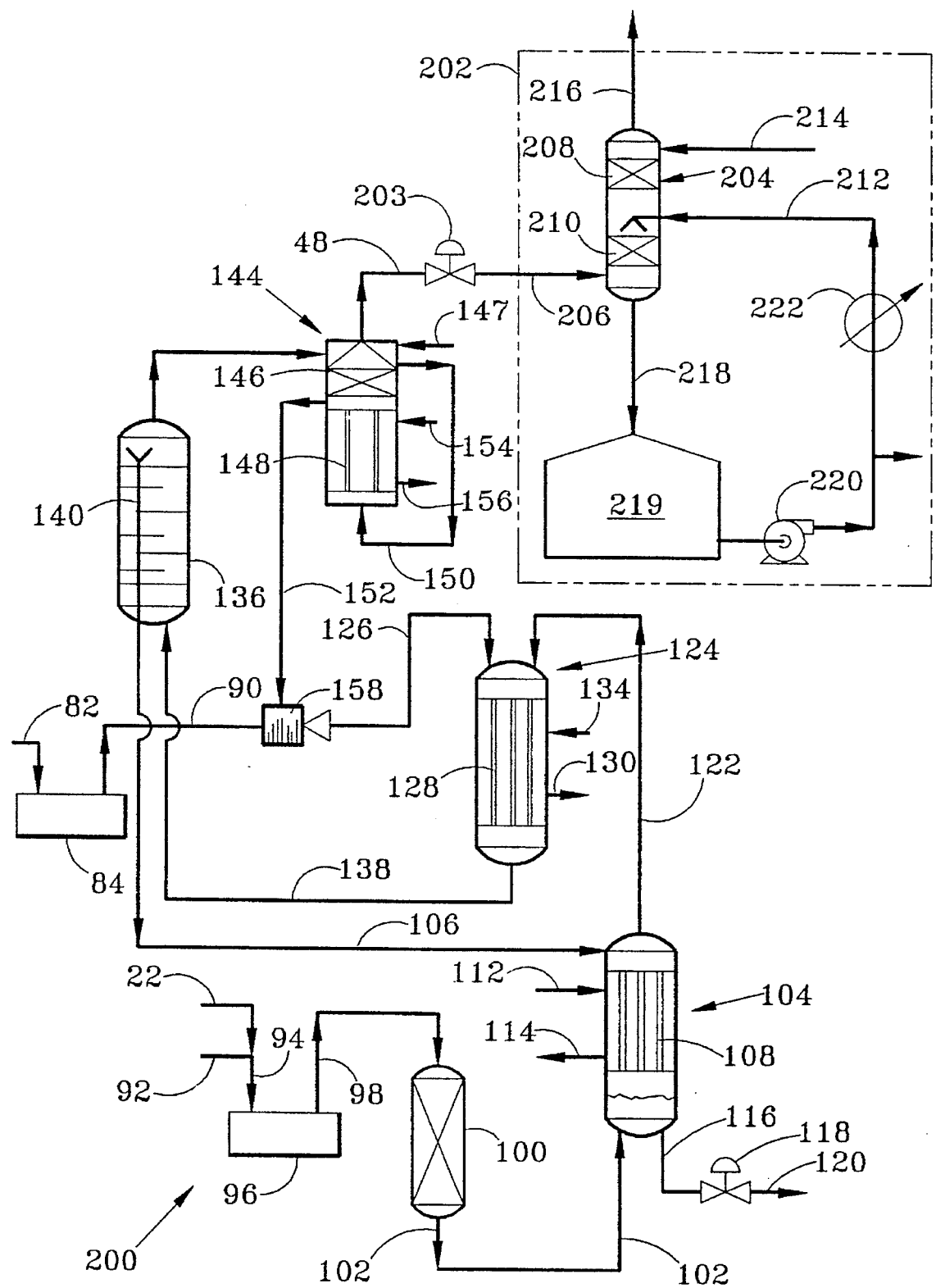
FIG. 2 (prior art) is a schematic diagram of a urea process of the prior art showing a medium pressure absorber and associated equipment used to reduce ammonia concentration of a urea synthesis unit purge stream for atmospheric venting.

Referring to FIGS. 1–2, wherein like numerals refer to like streams and equipment, an integrated ammonia/urea process 10 of the present invention uses a waste stream of a urea synthesis process 12 as a supplementary feedstock to an ammonia synthesis process 14.

As well known in the art, urea is made in a continuous process by the reaction of ammonia and carbon dioxide at an elevated temperature and pressure. Ammonia and carbon dioxide are combined directly in a liquid ammonia medium to form ammonium carbamate, followed in a is continuous fashion by dehydration of the carbamate to urea and water.

The ratio of ammonia to carbon dioxide will depend on the process being used. For the well known Stamicarbon process based on $CO_2$ stripping, a molar reactant ratio of about 2.8:1 of ammonia:carbon dioxide is suitable. In the Toyo Engineering ACES process based on $CO_2$ stripping, a molar ratio of about 4.0:1 of ammonia:carbon dioxide is suitable. In the Snamprogetti process based on $NH_3$ stripping, the normal ratio of ammonia:carbon dioxide in the feed is about 3.6:1. At a pressure in the range of 14–15 MPa and a temperature of 180°–195° C., conversion of about 50–70 percent of the $CO_2$ (limiting reactant) per pass is obtained.

Ammonia, as very well known, is typically made by catalytic combination of a hydrogen and nitrogen feedstock at elevated temperature and pressure. An ammonia syngas, comprising a desired stoichiometric ratio of hydrogen and nitrogen, is produced by reforming a natural gas feed in the presence of air and steam in a reforming furnace. As a byproduct of the reforming process, carbon dioxide is produced. Thus, it can be seen that ammonia production makes the starting materials necessary for urea production.

Referring more specifically to the ammonia process 14 of the present invention, atmospheric air introduced to an air compressor 16 through line 18 is compressed in two stages. Such air compressors typically employ steam drives, gas turbine drives or electrical motor drives (not shown). Part of the discharge from a first stage 20 is removed through line 22 for feed as passivation air in the urea process 12. The remainder of the first stage discharge is compressed by a second compression stage 24 and fed to a syngas production unit 26 through line 28. The oxidant stream in line 28 is usually initially preheated in heating coils 30 typically located in a furnace stack (not shown). Preheated oxidant is withdrawn through line 32.

The syngas unit 26 typically is made up of the primary reforming furnace 34 and a secondary autothermal reformer 36. A compressed hydrocarbon feed stream 38 typically comprising natural gas is mixed with steam introduced through line 40 and directed through line 42 to reaction coils (not shown) located in a radiant chamber (not shown) of the furnace 34. In the furnace 34, the hydrocarbon (methane) feed stream is preheated and reformed in the presence of the steam to produce hydrogen, carbon monoxide and carbon dioxide.

An effluent stream from the furnace 34 is directed through line 44 to the autothermal or secondary reformer 36 for further reforming reaction. However prior to autothermal or secondary reforming of the primary reformer effluent stream 44, a desired stoichiometric quantity of nitrogen is added as a component of the oxidant (e.g. air) stream 32.

Although the present invention is described herein by reference to the synthesis gas process as illustrated in FIG. 1 as an example, it is understood that the invention is equally applicable to other synthesis gas production schemes, such as, for example, processes wherein the primary furnace is heated by the effluent from the autothermal reformer, as in U.S. Pat. No. 5,011,625 to Le Blanc and U.S. Pat. No. 4,479,925 to Shires et al. which are hereby incorporated herein by reference.

In the practice of the present invention, a high pressure urea synthesis purge stream withdrawn from urea synthesis cycle 46 through line 48 is combined with the preheated oxidant stream 32 for feed through line 50 to the autothermal reformer 36. The urea synthesis purge stream 48 comprises primarily nitrogen with minor amounts of oxygen, ammonia and $CO_2$. The oxygen, nitrogen and $CO_2$ from stream 48 are ordinary reactants and/or inerts in the reformers 36; the small amount of ammonia present is believed to be converted to nitrogen and hydrogen, without adversely affecting the reforming or shift conversion reactions.

An effluent stream removed from the autothermal or secondary reformer 36 through line 52 is passed through to heat recovery unit 54, a shift reactor 56 for conversion of CO to hydrogen, a $CO_2$ recovery unit 58 and to a methanation unit 60 for removal of residual CO, $CO_2$, water and other undesirable components.

A syngas stream, thus finished, is introduced through line 62 as makeup syngas to an ammonia synthesis cycle 64. In an exemplary ammonia synthesis process as illustrated in FIG. 1, the makeup syngas stream 62 is compressed by a two stage ammonia synthesis compressor 66. Prior to compression, however, the makeup syngas stream 62 is combined with a hydrogen stream 68 separated from an ammonia synthesis cycle purge stream 70 by an ammonia purge gas hydrogen recovery unit 72.

Effluent gas from a first compression stage 74 is combined with ammonia recycle gas introduced through line 76. A combined ammonia synthesis gas stream is then compressed to the operating pressure of ammonia converter 78 by the second compression stage 80. Effluent gas from the ammonia converter 78 is introduced through line 82 to a cryogenic ammonia recovery unit 84. Syngas separated from ammonia product is recycled through line 86 except for the purge stream which is removed through line 70 for feed to the purge hydrogen recovery unit 72. A hydrogen lean purge stream 88 is removed from the hydrogen recovery unit 72 for use as a fuel gas. An ammonia feed stream is directed to the urea plant 12 through line 90.

It is understood that the present invention is not limited by the manner of ammonia synthesis of which a conventional process scheme is described above. Other process arrangements could be used. Examples of other ammonia synthesis processes can be found in U.S. Pat. No. 4,568,530 to Mandelik et al.; U.S. Pat. No. 4,568,531 to van Dijk et al; and U.S. Pat. No. 4,568,532 to Benner et al. which are hereby incorporated herein by reference. Further disclosure regarding ammonia converter design and catalyst composition can be found in U.S. Pat. No. 4,163,775 to Foster et al.; and U.S. Pat. Nos. 4,122,040 and 4,055,628 to McCarroll et al. which are hereby incorporated herein by reference.

Turning to the urea process 12, the corrosion passivation air stream 22 is preferably withdrawn from the first stage 20 of the ammonia process air compressor 16 as mentioned above, and combined with a carbon dioxide makeup stream introduced through line 92 for feed to the urea synthesis cycle 46. The carbon dioxide makeup stream 92 is preferably supplied as a product stream of the $CO_2$ recovery unit 58. Thus, carbon dioxide makeup 92 to the urea synthesis cycle 46 generally has a maximum hydrogen concentration of about 1.3 volume percent (40° C., 1.667 KPa,a).

A combined stream of passivation air and makeup $CO_2$ is directed through line 94 to a $CO_2$ compressor 96. The $CO_2$ compressor 96 which is typically a multi-stage centrifugal unit compresses the combined stream 94 to a pressure on the order of 15 MPa(a). A compressed $CO_2$-containing stream is then withdrawn through line 98 and directed to a hydrogen removal unit 100. The hydrogen present in the makeup $CO_2$ is removed by catalytic combustion in the hydrogen converter 100 to a concentration less than about 10 ppmv wherein a portion of the air provides oxygen for the conversion process. An essentially hydrogen-free $CO_2$ makeup stream containing air is removed via line 102.

The compressed and dehydrogenated $CO_2$/air stream 102 is preferably directed to a stripping heat exchanger 104 operated at urea synthesis cycle pressure. The stripping heat exchanger 104 removes unreacted ammonia and carbamate from a liquid urea synthesis effluent stream supplied via line 106. The stripper 104 typically comprises a vertical falling-film heat exchanger wherein vapor-liquid contact occurs at the surface of the tubes 108. The stripper 104 is reboiled by process steam supplied shell-side via line 112 and condensate is removed via line 114. An aqueous urea product stream lean in ammonia and carbon dioxide is withdrawn from the stripper 104 via line 116. The urea product stream 116 is subsequently depressurized by letdown valve 118 for feed through line 120 to a urea purification unit (not shown). The condensate stream 114 is typically recycled to a boiler.

Makeup carbon dioxide containing minor amounts of air and ammonia is removed overhead from the stripper 104 and directed via line 122 to a carbamate shell and tube condenser 124 generally operated at urea synthesis cycle pressure. In the carbamate condenser 124, a high pressure liquid makeup ammonia stream introduced through line 126 and the carbon dioxide stream 122 are contacted tube-side under cooling conditions to produce a condensed carbamate reaction product. Concurrently, the heat of carbamate formation is dissipated into boiler feed water pumped shell-side through line 130 to the condenser 124. The steam produced in the condenser 124 is withdrawn through line 134 for plant-wide utility use. A condensed carbamate effluent stream is removed as bottoms from the condenser 124 for feed to a urea reactor 136 via line 138.

The urea reactor 136 is operated at suitable urea synthesis conditions and typically comprises a large vertical vessel having a residence time necessary to facilitate dehydration of liquid carbamate to urea and water which is a slower reaction than carbamate formation. The reactor 136 is run at substantially plug-flow conditions with limited internal mixing. A product effluent stream comprising aqueous urea and unreacted carbamate is withdrawn from an upper portion of the reactor 136 via a siphon line 140 and directed through line 106 to the stripper 104 as mentioned above.

A vapor purge stream comprising primarily air introduced to the reactor 136 in the makeup $CO_2$ is removed overhead from the reactor 138 via line 142. The purge stream 142 is scrubbed in a high pressure scrubber 144 operating at about the pressure of the urea synthesis cycle to substantially remove residual carbon dioxide and ammonia therefrom. The high pressure scrubber 144 comprises an upper packed section 146 and a lower heat exchanger section 148. The stream 142 is initially passed around the upper packed section 146 through an explosion dome in indirect heat exchange, and then into the lower heat exchange section 148 where ammonia and $CO_2$ are condensed to form carbamate. The heat of carbamate formation is dissipated to tempered cooling water circulated to a shell side of the exchanger section 148 via lines 154, 156. Condensate and non-condensed vapors pass up from the lower heat exchanger section 148 to the lower end of the upper packed section 146. The vapors are contacted countercurrently as they rise through the packed section 146 with carbamate solution introduced near the top of the packed section 146 via line 147 to substantially remove residual ammonia and $CO_2$. Stream 147 is obtained, for example, as recycle carbamate condensed from recovery of urea product from stream 120, but can be any suitable aqueous stream. The purge stream 142 thus substantially scrubbed of residual ammonia and $CO_2$ is withdrawn through line 48 as mentioned above for feed to the autothermal reformer 36. Carbamate solution is withdrawn from the bottom of the packed section 146 through line 152 for return to the urea reactor 136 via the carbamate condenser 124.

The carbamate return stream 152 is preferably drawn from the high pressure scrubber 144 to the high pressure condenser 124 using an educator 158 employing the high pressure liquid ammonia makeup stream 90 as the motive fluid. An eductor effluent stream comprising the ammonia makeup stream 90 and the return carbamate stream 152 is directed to the carbamate condenser 124 through line 126.

In an alternative embodiment of the present invention, the ammonia makeup stream 90 can be introduced to the high pressure stripper 104 via line 160 to strip $CO_2$ and carbamate from the urea synthesis effluent stream 106, in which case, the $CO_2$/air makeup stream 102 is directed from the hydrogen combustor 100 to the reactor 136 via line 162, as in the Snamprogetti process.

For comparison to the practice of a prior art process 200, as seen in FIG. 2, the purge stream 48 is further scrubbed at a lower pressure by a medium pressure scrubbing unit 202 to condition the purge stream 48 comprising air and low concentrations of ammonia and $CO_2$ for atmospheric disposal. The purge unit 202 employs plant condensate to further reduce the remaining ammonia content in the purge gas 48. The purge stream 48 is let down in pressure to about 0.4 MPa(a) by a letdown valve 203 and introduced to a medium pressure absorber 204 via line 206. The medium pressure absorber 204 comprises a vertical shell having two packed sections 208, 210. In packed section 210, the low pressure purge gas 206 is countercurrently contacted with a spray of plant condensate introduced through line 212. In packed section 208, the effluent gas rising from the packed section 210 is countercurrently contacted with a water stream from a condensate cooler (not shown) is introduced through line 214. An ammonia-lean stream of nitrogen and oxygen is obtained via line 216 for atmospheric discharge.

Condensate effluent is withdrawn from the bottom of the absorber 204 via line 218 for circulation to a holding tank for treatment of the residual ammonia such as by neutralization with a mineral acid. The condensate, thus treated, is recirculated by pump 220 to the medium pressure absorber 204 following cooling against cooling water in a heat exchanger 222. The entire purge unit 202 is desirably eliminated with the present invention.

The benefits of the present process are illustrated by reference to the following example:

EXAMPLE

The impact of integrating the purge stream 48 from the urea plant high pressure scrubber 144 with the ammonia plant secondary reforming section 36 for a 1500 metric tons per day (MTPD) urea plant and a 1000 MTPD ammonia plant are analyzed by computer simulation. In addition, standard cost estimating programs are conducted to calculate potential cost savings in utilities and capital equipment.

No adverse impact in the operation of the secondary reformer 36 is seen. The purge recycle stream 48 contains approximately 78.8 mole percent nitrogen, 9.8 mole percent oxygen, 8.0 mole percent ammonia, 3.1 mole percent $CO_2$, 0.3 mole percent water, and less than 10 ppmv hydrogen (the hydrogen is from the $CO_2$ stream 62 after combustion in the hydrogen combustion unit 100). However, assuming as much as 100 ppmv hydrogen remains in the purge recycle stream 48, combustion of hydrogen would increase the temperature of the process air (to the autothermal reformer 36) only about 0.3° C. maximum. Savings in the ammonia plant include an approximately 3.2% reduction in power consumption of the air compressor 16 and reduced cooling water circulation of the air compressor steam drive (not shown) due to a lower steam requirement.

There is no adverse impact on the urea plant. Capital equipment savings include elimination of the medium pressure absorber 204 and ancillary equipment such as condensate pumps and coolers, control valves and stainless steam piping. However, elimination of the medium pressure absorber 204 requires the addition of a centrifugal pump (not shown) of estimated capacity of 20 m³/hr to feed ammonia water solution from a tank to an atmospheric absorber (not shown) for treatment of other ammonia-containing vent streams.

Utilities cost savings in the present integrated plant in one year are shown in Table 1. Utilities savings for a three year period approximately $252,000. A capital cost saving is given in Table 2. Overall capital saving is estimated at $616,000.

TABLE 1

| Source | Amount | Savings ($/yr) |
|---|---|---|
| Ammonia unit | | |
| Steam for air compressor 16 | 2.9 MMBTU/hr | 58,000[a] |
| Urea unit | | |
| Power for feed pump to medium pressure absorber 204 | 17 KW | 6,800[b] |
| Condensate consumption in medium pressure absorber 204 | 1.5 MT/hr | 6,000[c] |
| Ammonia/Urea integrated plant | | |
| Cooling water to surface condenser (not shown) of air compressor 16 steam drive unit and medium pressure absorber condensate feed cooler 222 | 58 M³/hr | 13,900[d] |

[a]$2.5/MMBTU.
[b]$0.05/KWH.
[c]$0.5/MT.
[d]$0.03/M³.

TABLE 2

| Equipment | Capital Savings ($) |
|---|---|
| Medium pressure absorber 204 with packing | 121,000 |
| Medium pressure absorber feed cooler 222 | 19,000 |
| Medium pressure absorber feed pump and spare 220 | 50,000 |
| Carbamate transfer pump and spare (not shown) | −40,000 |
| Piping, instrumentation, electrical and civil work (not shown) | 466,000 |

The present integrated ammonia/urea process is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

We claim:

1. An integrated ammonia and urea plant, comprising:

an ammonia syngas unit including primary and autothermal reformers, a shift converter, and a $CO_2$ removal unit, for reacting a hydrocarbon feedstock with steam and air to form a $CO_2$ stream and a syngas makeup stream comprising hydrogen and nitrogen;

an ammonia conversion unit including a synthesis loop for mixing a recycle stream with the syngas makeup stream to form an ammonia converter feed stream, feeding the ammonia converter feed stream to an ammonia synthesis reactor, recovering an ammonia stream from effluent from the synthesis reactor, recovering a purge stream from the effluent stream, and forming the recycle stream;

a urea unit for reacting the $CO_2$ stream with the ammonia stream to form urea at a relatively high pressure above about 14 MPa in the presence of a passivating amount of oxygen and a minor amount of nitrogen, the urea unit including a high pressure scrubber for separating oxygen and nitrogen from a urea-containing stream to form a high pressure nitrogen stream above about 14 MPa containing minor amounts of oxygen, $CO_2$ and ammonia; and a line for introducing the high pressure nitrogen stream with compressed air to the autothermal reformer.

2. The integrated plant of claim 1, wherein the high pressure nitrogen line feeds directly into a compressed air line downstream of an air compressor wherein the pressure in the high pressure nitrogen line is greater than the pressure of the compressed air line.

3. The plant of claim 2, wherein the urea unit is free of ammonia removal equipment for treating the high pressure nitrogen stream and free of atmospheric vents for nitrogen from the high pressure scrubber.

4. A method for integrating the operation of ammonia and urea plants comprising an ammonia syngas unit including primary and autothermal reformers, a shift converter, and a $CO_2$ removal unit, for reacting a hydrocarbon feedstock with steam and air to form a $CO_2$ stream and a syngas makeup stream comprising hydrogen and nitrogen; an ammonia conversion unit including a synthesis loop for mixing a recycle stream with the syngas makeup stream to form an ammonia converter feed stream, feeding the ammonia converter feed stream to an ammonia synthesis reactor, recovering an ammonia stream from effluent from the synthesis reactor, recovering a purge stream from the effluent stream, and forming the recycle stream; a urea unit for reacting the $CO_2$ stream with the ammonia stream to form urea at a relatively high pressure in the presence of a passivating amount of oxygen and a minor amount of nitrogen, the urea unit including a high pressure scrubber at a pressure above 14 MPa for separating oxygen and nitrogen from a urea-containing stream to form a high pressure nitrogen stream at a pressure above 14 MPa containing minor amounts of oxygen, $CO_2$ and ammonia; comprising the step of: introducing the high pressure nitrogen stream with compressed air to the autothermal reformer.

5. The ammonia/urea integration method of claim 4, wherein the high pressure nitrogen stream supplies at least 1 percent of the nitrogen supplied to the autothermal reformer.

6. The ammonia/urea integration method of claim 5, wherein the urea unit is free of atmospheric venting of process nitrogen streams.

7. The ammonia/urea integration method of claim 4, wherein the high pressure scrubber is operated at a higher pressure than the autothermal reformer, and the high pressure nitrogen stream is fed directly into a compressed air line downstream from a discharge of an air compressor and upstream from the autothermal reformer.

8. The ammonia/urea integration method of claim 7, wherein the high pressure nitrogen stream contains at least 70 mole percent nitrogen, 1–15 mole percent oxygen, 1–15 mole percent ammonia, 1–10 mole percent $CO_2$, up to 3 mole percent water, and less than 100 ppmv hydrogen.

* * * * *